US006789885B1

(12) United States Patent
Michele et al.

(10) Patent No.: US 6,789,885 B1
(45) Date of Patent: Sep. 14, 2004

(54) CONFIGURATION FOR FORMING A VENTILATION APERTURE

(75) Inventors: Helmut Michele, Castrop-Rauxel (DE); Dirk Klein, Hagen (DE); Peter Busch, Bochum (DE)

(73) Assignee: ARTECH GmbH design + production in plastic, Portmund (DE)

( * ) Notice: Subject to any disclaimer, the term of this patent is extended or adjusted under 35 U.S.C. 154(b) by 144 days.

(21) Appl. No.: 09/661,121

(22) Filed: Sep. 13, 2000

(30) Foreign Application Priority Data

Sep. 14, 1999 (DE) .......................................... 199 43 949

(51) Int. Cl.[7] .......................... B41J 2/175; F04F 10/00; A61M 5/14

(52) U.S. Cl. ........................... 347/86; 137/43; 604/256

(58) Field of Search .............................. 347/85, 86, 87; 137/43, 247.11, 247.41, 384; 454/254, 270, 301, 302, 289; 604/256

(56) References Cited

U.S. PATENT DOCUMENTS 3,953,862 A * 4/1976 Amberntsson et al. ........ 347/93
4,785,314 A 11/1988 Terasawa et al. ........... 346/140
5,949,461 A * 9/1999 Jones et al. .................... 347/87
6,273,562 B1 * 8/2001 Deshmukh .................... 347/86

FOREIGN PATENT DOCUMENTS

| | | | |
|---|---|---|---|
| DE | G 80 34 018.7 | 5/1984 | ........... B65D/47/32 |
| EP | 0 598 481 | 5/1994 | ............ B41J/2/175 |
| EP | 685 339 | 12/1995 | ............ B41J/2/175 |
| JP | 8-300673 | 11/1996 | ............ B41J/2/175 |

* cited by examiner

*Primary Examiner*—Anh T. N. Vo
(74) *Attorney, Agent, or Firm*—Hoffman, Wasson & Gitler, PC

(57) ABSTRACT

The invention pertains to a configuration for forming a ventilation aperture having a small cross section, whereby a sealing part is placed in a passageway and the ventilation aperture is formed between the sealing part and the inner wall of the passageway. In order to simplify manufacturing and, in particular, make possible the use of injection-molded plastic parts throughout, the invention suggests that the sealing part should have a cylindrical stopper that is made of an elastically deformable material and can be inserted into the passageway, and has in its surface shell at least one axially continuous, channel-like depression, the outside diameter of which, when in the unstressed state, is oversized in comparison with the inside diameter of the passageway.

15 Claims, 2 Drawing Sheets

CONFIGURATION FOR FORMING A VENTILATION APERTURE

FIELD OF THE INVENTION

Figure 1:
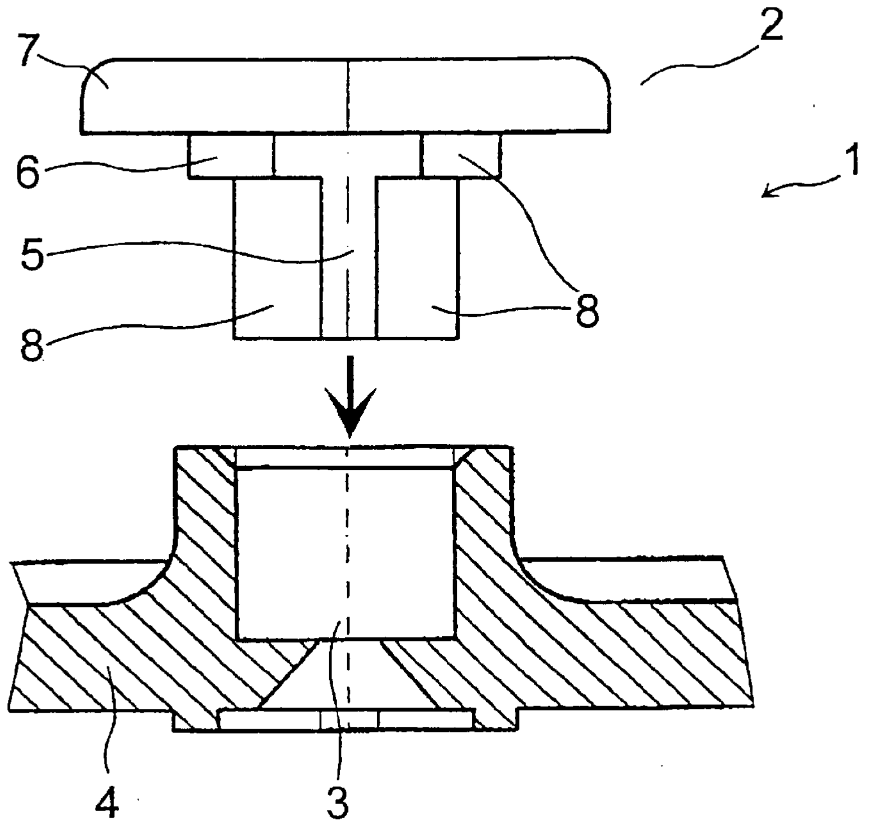

The invention pertains to a configuration for forming a ventilation aperture having a small cross section, whereby a sealing part is placed in a passageway and the ventilation aperture is formed between the sealing part and the inner wall of the passageway. In particular, this pertains to the ventilation aperture in the ink tank of an inkjet printer ink cartridge.

PRIOR ART

In order to equalize pressure with the environment, liquid-filled containers from which liquid is to be drawn off during operation have a ventilation aperture to allow ambient air to flow in, since the liquid in the container would otherwise form a restraining negative pressure. This is especially applicable for the ink tanks used in ink cartridges for inkjet printers. A uniform, well-defined ink supply to the inkjet printhead presupposes pressure relationships within narrowly defined tolerance ranges. This means that an amount of air corresponding to the amount of ink that was withdrawn should flow in through the ventilation aperture as smoothly as possible.

Ventilation apertures on ink tanks have a relatively small cross section, on the order of magnitude of 1 $mm^2$, and are specifically, distributed over several correspondingly smaller individual apertures, if possible. In terms of quality that is as consistent as possible for ink tanks of this type, the uniform maintenance of the defined passage cross section is especially important, and specifically, and also especially in large-scale production. In view of that fact, it is of critical importance that the ventilation apertures can be reproduced as exactly as possible, and that they are as inexpensive as possible to produce, i.e., with little technical effort.

With regard to the state of the art in terms of the production of ventilation apertures, a design has already been described in EP 0 598 481 A1 in which a sealing part in the form of a sphere is pressed into a passageway in the housing wall of the ink tank. The passageway is provided with radially protruding ribs in order to hold the sphere. Between these ribs a narrow annular gap exists between the sphere and the inner wall of the passageway, which defines the ventilation aperture. This configuration is also known as a “bubble generator” that provides for the release of air bubbles for pressure equalization with the ambient atmosphere in any position of the ink tank, i.e., even when ink is resting on the ventilation aperture.

The bubble generator mentioned above has the advantage of relatively reliable functioning. To achieve this, however, high-precision manufacturing of the housing is required, and of the passageway with the apertures in particular. This is especially true of the sphere that is placed inside, and for that reason a highly accurate glass sphere is used. A simple, formed plastic part cannot be used in this configuration, which of course results in increased labor and costs.

Proceeding from the state of the art as described above, the task of the present invention is therefore to suggest an option for configuring a ventilation aperture that requires less manufacturing effort and cost, but nevertheless makes it possible to provide a ventilation aperture that can be reproduced with precision.

SUMMARY OF THE PRESENT INVENTION

To carry out this task, the invention suggests that, starting with the features mentioned at the beginning, the sealing part should have a cylindrical stopper that is made of an elastically deformable material and can be inserted into the passageway, that has in its surface shell at least one axially continuous, channel-like depression, and the outside diameter of which, when in the unstressed state, is oversized in comparison with the inside diameter of the passageway. The characteristic feature of the configuration in accordance with the invention results from the interaction of its individual parts. Specifically, the fact that the cylindrical stopper is oversized relative to the inside diameter of the passageway in the wall means that its outside diameter is either actually larger than the inside diameter of the passageway in the wall or is at least equal in size, so that a press fit is provided whereby the stopper can be pressed into the aperture through the use of axial pressing force. Assuming that the passageway has no give in the radial direction, the elastically deformable material of the stopper will deform when it is pressed into place. While the elastic material would be able to deflect only in the axial direction in the case of a solid cylindrical stopper, in the design according to the invention it is squeezed radially and in the circumferential direction into the channel-like depressions running along the outside, so that its free passage cross section becomes smaller than when in the unstressed state. As a result of the well-defined matching of the diameters or cross sections of the passageway, the stopper, and the depression or depressions, passage cross sections as small as desired can be predetermined for the ventilation aperture, which corresponds to the cross section of the depressions squeezed together when the stopper is pressed into place.

A particular advantage of the design in accordance with the invention lies in the fact that for the first time, both the wall with the passageway and the sealing piece in the form of the stopper according to the invention can be made as injection-molded formed plastic parts that can be made available with little manufacturing effort or cost. The passageway in the wall, of the ink container of an ink cartridge for an inkjet printer, for example, merely has a round cross section with no ribs or additional depressions as is the case in the state of the art, so that it can be reproducibly created with sufficient high precision using common manufacturing methods. For the sealing piece in accordance with the invention, i.e., the stopper provided with the channel-like depressions, the same holds true as a matter of principle. Specifically, its standard cylindrical form is modified only by the axially continuous channels or grooves that are formed into its outside, which, taking into consideration modern plastic injection-molding manufacturing techniques, can also be carried out with markedly little effort. Sufficiently high precision and reproducibility is likewise assured in every case. Specifically, during the manufacturing of the stopper the depressions are given a larger open cross section than is necessary later for the ventilation apertures formed from it, since the adjustment of this nominal cross section takes place—as has been described earlier—only when it is pressed into the passageway in the housing. The larger open cross section during the manufacturing of the depressions simplifies production when conventional injection molding techniques are used.

In comparison with the state of the art, the use of a sealing piece made of injection-molded plastic has the added advantage that no additional parts such as glass spheres, etc., have to be purchased in addition, and the manufacturing is simpler and less expensive as a result.

Moreover, the design according to the invention has the special advantage that for a given diameter of the passageway in the wall, through the design of the cross section, the depth, the shape and the number of depressions, the amount of oversize, and the choice of elastic material, it is possible to adjust the properties of the ventilation configuration, and thus the best possible adaptation to the given requirements can take place.

The entire sealing part, including stopper, is manufactured as a formed plastic part, made, for example, of polypropylene, as an injection-molded part.

Preferably, the channel-like depression is given a V-shaped cross section. This shape is easy to manage in terms of manufacturing technology, and is also especially favorable in terms of the deformation while being pressed into place in the passageway in order to form a fine gap with a defined cross section. The depression can also have a U-shaped or other cross section as well.

Preferably, the stopper is provided with a plurality of depressions distributed symmetrically over its circumference. The characteristics of the ventilation aperture can be influenced and optimized within wide limits by the number and cross section of the individual depressions.

An advantageous further development of the invention provides that a discharge section having a larger diameter than the stopper is formed axially onto the stopper, whereby the channel-like depression passes axially through the discharge section. This discharge section is preferably mounted on the stopper as one piece by forming a shoulder on the latter, so that it forms a limit stop when the stopper is pressed into the passageway, i.e., it protrudes from the passageway. As a result of the fact that the depressions are drawn axially through the discharge section, free inward flow in the direction of the discharge section is guaranteed even if the latter is covered, for example.

A head section of a larger diameter is advantageously formed axially onto the stopper as one piece. It serves as an insertion limiter when pressed into the passageway. As a further development, this head section can also be formed axially onto the discharge section, in which it is at least as large in diameter as the latter. As a result of the channel-like depressions that end underneath the underside of the head, discharge openings that are directed radially outward are formed, which for that reason are especially reliable in operation because their simultaneous blockage is practically impossible.

The invention also includes the method for manufacturing a ventilation aperture of small cross section in a container wall, specifically, in a ink tank of an inkjet printer as was explained in some detail above. This method makes particular use of knowing how to manufacture an easily produced depression of larger cross section when the stopper is being pressed oversized into a predetermined wall passageway, whereby the depression is squeezed together to the nominal dimension of the cross section of the ventilation aperture while reducing the cross section.

The fastening of the stopper, which, like the wall, is made of a thermoplastic, can be carried out very easily by means of ultrasonic welding, whereby only an ultrasonic excitation of the container wall must be carried out such as is already being done, for example, when the container wall is placed onto and ultrasonically welded to a container. Because of the mass ratios of wall and stopper, they are placed into relative movement, as a result of which they are nondetachably welded to one another.

DETAILED DESCRIPTION OF THE DRAWINGS

Figure 2:
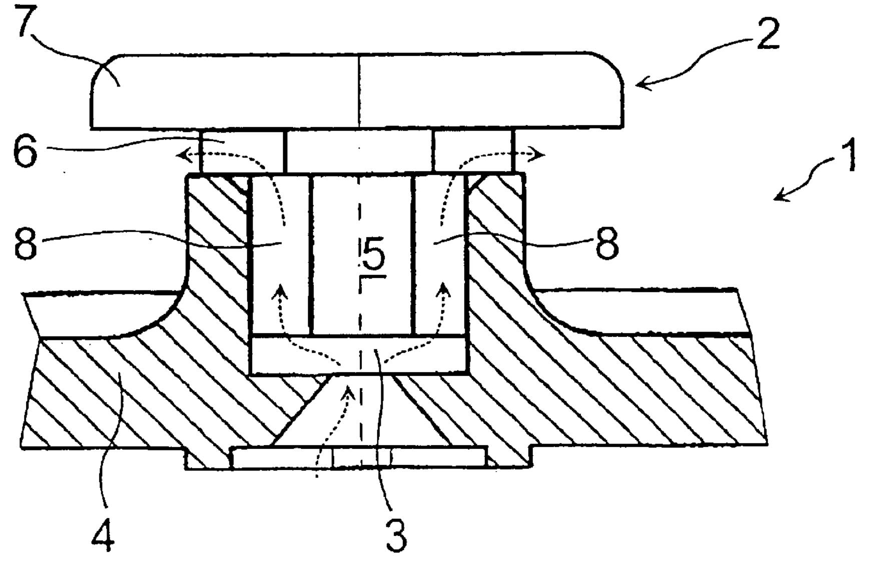
Figure 3:
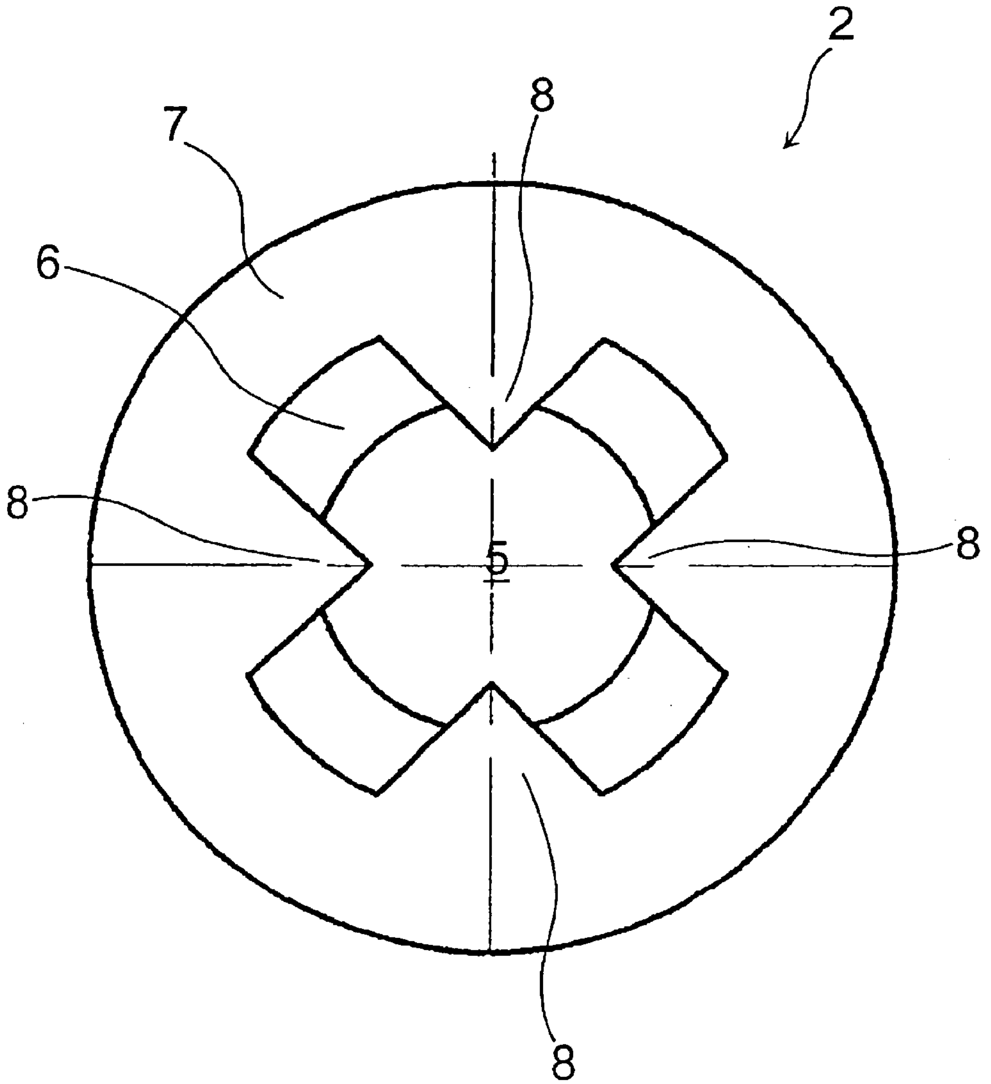

In the following, an embodiment of an ventilation configuration in accordance with the invention is explained in more detail with the aid of the drawings. Specifically shown are:

FIG. 1: A ventilation configuration according to the invention, in disassembled state;

FIG. 2: A ventilation configuration according to the invention in FIG. 1, in assembled state;

FIG. 3: An axial view of the sealing piece according to FIG. 1 and FIG. 2.

DETAILED DESCRIPTION OF A PREFERRED EMBODIMENT

The ventilation configuration in accordance with the invention is shown in side section view in FIG. 1 and FIG. 2, once in the disassembled state (FIG. 1) and once in the assembled state (FIG. 2), whereby it is provided in its entirety with reference number 1. It is formed from a sealing piece 2 and a passageway 3 in the wall 4 of an ink tank (not shown in more detail) of an ink cartridge for an inkjet printer. As is shown in the drawings, the sealing piece 2 is pressed into the passageway 3 from the inside of the container.

The passageway 3, which is shown in section, is cylindrical in shape with a defined inside diameter and smooth inside wall. It is formed into the wall 4, which is an injection-molded plastic part.

The sealing piece 2 is also a one-piece injection-molded plastic part, made, for example, of polypropylene. It has a cylindrical stopper 5 that has an axial discharge section 6 formed towards the top of the drawing, and head section 7 formed onto that. The head 7 has a larger diameter than the discharge section 6, which has a larger outside diameter than the stopper 5.

The stopper 5 is provided with a total of four channel-like, axially continuous depressions 8 that are evenly distributed around its outer circumference, and their configuration can be seen especially well in the axial view per FIG. 3. The V-shaped cross section can also be seen there.

The stopper 5 is oversized relative to the passageway 3, i.e., its diameter has the same size as the inside diameter of the passageway 3, or it can be as much as 0.1 mm larger, for example, or even larger.

When the sealing piece 2 with the stopper 5 is pressed into the passageway 3—as is indicated by the arrow in FIG. 1—up to the state shown in FIG. 2 and the discharge section 6 lies on the upper edge of the passageway 3, the stopper 5 is elastically deformed. As a result of the deflection of the material radially and in the circumferential direction, the cross section of the depressions 8 is squeezed into the final cross section of the ventilation apertures. In the assembled state as shown in FIG. 2, these ventilation apertures are formed by the depressions 8 and the associated wall sections of the passageway 3. The ventilation apertures end in discharge section 6, so that ambient air from outside can flow into the interior of the ink tank as indicated by the dotted arrows.

Both the sealing piece 2 and the wall 4 with the passageway 3 are injection molded plastic parts that are simple to manufacture. As a result of the number and the shape and dimensions of the depressions 8 plus the oversize of the stopper 5 relative to the inside diameter of the passageway 3, the desired ventilation cross section can be made variable with little manufacturing effort and cost.

The fastening of the sealing piece 2 is advantageously carried out by setting the entire wall into ultrasonic vibration. As a result of the relative movement, a welding of the outer circumference of the stopper 5 to the inner wall of the passageway 3 takes place.

What is claimed is:

1. A configuration for forming a ventilation aperture having a small cross section, comprising a sealing part placed in a passageway and the ventilation aperture formed between the sealing part and the inner wall of the passageway, said sealing part having a cylindrical stopper that is made of an elastically deformable material and can be inserted into a passageway, which has at least one axially continuous, channel-like depression, for which the outside diameter in an unstressed state is oversized in comparison with the inside diameter of the passageway, said sealing part compressed by said passageway to reduce the cross section of said depression.

2. The configuration according to claim 1, wherein said sealing part is a formed plastic part.

3. The configuration according to claim 2, characterized in that the sealing part is an injection-molded part.

4. The configuration according to claim 1, characterized in that the channel-like depression has a V-shaped cross section.

5. The configuration according to claim 1, characterized in that the channel-like depression has a U-shaped cross section.

6. The configuration according to claim 1, wherein said stopper is has a plurality of depressions distributed symmetrically around its circumference.

7. The configuration according to claim 1, wherein that formed axially onto said stopper is a discharge section that has a larger outside diameter than said stopper, in which said channel-like depression passes axially through said discharge section.

8. The configuration according to claim 1, wherein a head section with a larger diameter is formed axially onto said stopper as one piece.

9. The configuration according to claim 1, wherein said head section is formed axially onto said discharge section and is at least as large in diameter as the latter.

10. The configuration according to claim 1, wherein said passageway is located in a wall of a container.

11. The configuration according to claim 10, wherein said container is a ink tank of an inkjet printer ink cartridge.

12. A method for the manufacturing of a ventilation aperture of small cross section in a container wall, comprising inserting a sealing part into a passageway in the container wall, the sealing part made of elastically deformable material, forming at least one axially continuous, channel-like depression in said sealing part, and the outside diameter of the sealing part, when in the unstressed state, is oversized in comparison with the inside diameter of the passageway, pressing the sealing part into the passageway, and reducing the cross section of the depression in order to form said ventilation aperture.

13. The method according to claim 12, further comprising ultrasonically welding said stopper in said passageway.

14. A configuration for forming a ventilation aperture having a small cross section, comprising a sealing part placed in a passageway, said sealing part having a stopper that is made of an elastically deformable material and can be inserted into said passageway, said stopper having a top, a bottom and a sidewall, and at least one channel-like depression in said sidewall to form a ventilation aperture between the sealing part and the side of the passageway.

15. The configuration of claim 14, wherein said sealing part is welded to said passageway.

* * * * *